United States Patent [19]

Hara et al.

[11] Patent Number: 4,657,691
[45] Date of Patent: Apr. 14, 1987

[54] COMPOSITION FOR CLEANSING AND WIPING SKIN

[75] Inventors: Kenji Hara, Ichikaimachi; Yasuteru Eguchi, Utsunomiya, both of Japan

[73] Assignee: KAO Corporation, Tokyo, Japan

[21] Appl. No.: 842,160

[22] Filed: Apr. 25, 1986

Related U.S. Application Data

[62] Division of Ser. No. 615,761, May 31, 1984, abandoned.

[30] Foreign Application Priority Data

Jun. 8, 1983 [JP] Japan ................................ 58-102505

[51] Int. Cl.$^4$ ............................................. C11D 17/00
[52] U.S. Cl. .................................................. 252/91
[58] Field of Search ...................... 252/91, 89.1; 106/8, 106/9

[56] References Cited

FOREIGN PATENT DOCUMENTS 14509 8/1980 European Pat. Off. .

OTHER PUBLICATIONS

Derwent Abstract Accession No. 81-90130D/49, Japanese Pat. No. J56136899, Oct. 26, 1981.
Derwent Abstract Accession No. 81-59652D/33, Japanese Pat. No. J56079613A, Jun. 30, 1981.

Primary Examiner—Amelia B. Yarbrough
Attorney, Agent, or Firm—Oblon, Fisher, Spivak, McClelland & Maier

[57] ABSTRACT

A composition for cleansing and wiping skin in the circumanal region which comprises at least one oil selected from the group consisting of jojoba oil, natural squalane and glycerin tri-2-ethylhexanoate.

The composition according to the invention is preferably used after excrement is wiped off with usual toilet paper and facilitates removal of excrement residues on the skin of circumanal region. Besides, when the composition is applied to the circumanal skin prior to defecation, it prevents excrement from sticking to the skin or makes excrement easy to be wiped off.

The composition may be sprayed on conventional toilet paper or impregnated into nonwoven fabric, cloth, paper etc. on application.

Such materials containing the composition according to the invention is effective in preventing any aggravation to hemorrhoids or the like.

6 Claims, 2 Drawing Figures

COMPOSITION FOR CLEANSING AND WIPING SKIN

This is a division of application Ser. No. 615,761, filed May 31, 1984, now abandoned.

BACKGROUND OF THE INVENTION (i) Field of the Invention

This invention relates to a composition for cleansing and wiping skin, and more specifically, to a cleansing and wiping composition which facilitates removal of excrement remaining on the skin of circumanal region after defecation when excrement is wiped off with usual toilet paper or the like and which, when applied to circumanal skin prior to defecation, makes it difficult for the excrement to stick to the skin during the subsequent defecation or makes it easy to wipe off the excrement from the skin and thereby keeps the circumanal region clean and prevents any aggravation to hemorrhoids or the like.

(ii) Description of the Prior Art

For the wiping and cleansing treatment of the anus following defecation, toilet paper is generally used. Bidets and other washing apparatus using warm water, and cleansing cotton are also used, but rarely. From the viewpoint of skin irritation or filth removal, washing with warm water is the most desirable. However, washing apparatus using warm water are expensive and require cumbersome handling, and therefore have not come into wide use yet. Cleansing cotton costs much per one use, feels cold and is disadvantageous in that it cannot be disposed in a flush toilet. For these reasons, the actual situation is that toilet paper and coarse toilet paper are most generally used in wiping the anus after defecation.

The skin in the circumanal region has small wrinkles and creases and hair, and those portions of excrement residues which have got into such minute parts can be wiped off only with difficulty. Furthermore, sticking excrement residues, after solidification, are difficult to remove.

On the other hand, regeneration products account for about 70% of toilet paper and coarse toilet paper which are generally used. Physically, they are rather tough and therefore crumpled soft prior to use, but even they may injure the skin, causing excoriation. Excrement residues sticking to the skin parovide sources of propagation of bacteria, and decomposition products and the like produced by bacteria promote aggravation of the injured skin or cause itching, eruption or sore of the circumanal region. To clean the circumanal region is very important also to general public from the public health standpoint. In particular, to babies having a delicate skin and bedridden old people or to those suffering from diseases of the anus, such as hemorrhoids, that is important. Such people having some or other skin lesions in the circumanal region are sensitive to stimuli to the skin in the circumanal region and easily feel a pain upon stimulation in said region. Consequently, they tend to reduce the wiping force, and the results are insufficient wiping and increase in excrement residues.

Some of those with hemorrhoids, for instance those with internal hemorrhoid or light archoptosia, must push back internal hemorrhoid or archoptosia protruding from the anus after defecation into the anus by their fingers. Such treatment is usually accompanied by pain and thus something which physically facilitates the pushing of internal hemorrhoid or archoptosia into the anus is desired.

SUMMARY OF THE INVENTION

Under these circumstances, the present inventors conducted intensive study so as to develop a composition for cleansing and wiping the circumanal region which might be used after defecation in a simple and easy manner, might remove, to a sufficient extent, excrement residues remaining after wiping with toilet paper, might keep the circumanal region clean and might give a smooth and refreshing feeling after use. As a result, they found that the above object can be attained by using a composition which comprises specified oils.

Thus, this invention provides a composition for cleansing and wiping the skin which comprises at least one oil selected from the group consisting of jojoba oil, squalane and glycerin tri-2-ethylhexanoate.

DETAILED DESCRIPTION OF THE INVENTION AND PREFERRED EMBODIMENTS

Figure 1:
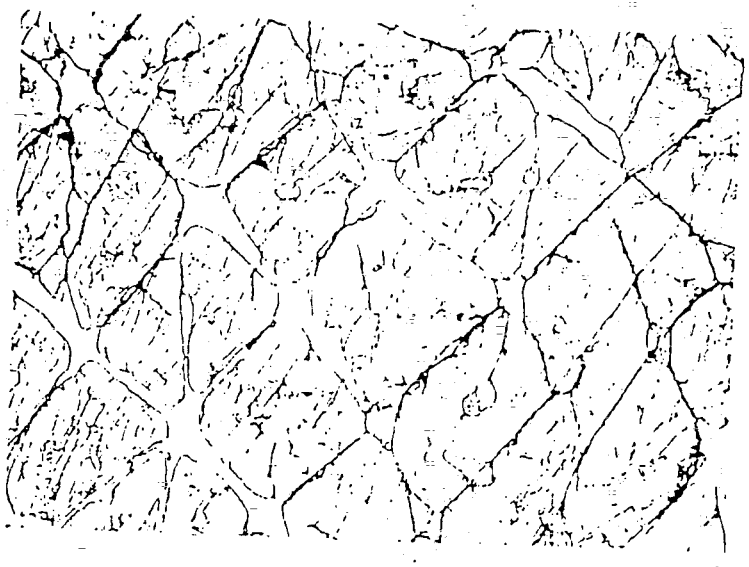
FIG. 1 is an illustration (photograph) indicating the skin condition after wiped with toilet paper produced from wastepaper.

It is necessary that oil to be used in this invention does not feel sticky, has a good affinity to the circumanal skin of the special region, does not stimulate skin and gives smooth and refreshing feeling of use. For such purposes, jojoba oil, squalane and glycerin tri-2-ethylhexanoate can be used. Liquid paraffin, olive oil and lanolin, which have been generally used in preparing baby oils and cosmetic oils conventionally, can not be favorably used for the circumanal region because they cause sticky feeling to remain.

The silicone oil to be used in accordance with the invention may be used either alone or in combination of two or more.

The cleansing and wiping composition according to the invention may, as desired, contain a microbicide, a pharmacologically active agent (e.g. antiinflammatory agent), an aroma chemical, and so forth, in addition to the above essential components.

For putting it to practical use, the cleansing and wiping composition according to the invention is filled in an appropriate container. It is especially convenient to use the composition in a sprayable form using either a propellant gas or a pressure-accumulating pump bottle.

The cleansing and wiping composition according to the invention is used, for example, in the following manne. Thus, after post-defecation wiping in the conventional manner with toilet paper or the like or on the occasion of diaper exchange, finish wiping is carried out with toilet paper or tissue paper sprayed several times with the composition according to the invention. The effects of this method of use can be further improved by wiping the circumanal region with tissue paper or toilet paper sprayed several times with the composition according to the invention after bathing or prior to defecation. In another mode of use, the composition according to the invention is directly applied to the cicumanal region, followed by wiping off with toilet paper or tissue paper, for instance.

Further, the composition according to the invention can be prepared or used in the form of an impregnated material. As a support material for impregnation, may for example be mentioned paper, nonwoven fabric, cloth, polymer film, sponge and foamed plastics, among which, paper and nonwoven fabric are especially preferred.

When the composition to be impregnated has large impregnation coefficient, the impregnation may be carried out either firstly immersing the support material into above-mentioned oils, followed by removing the excess oil by a pressurizing means etc., or directly spraying the oils to the support material. On the other hand, when the composition has small impregnation coefficient, similar procedures can be carried out but using mentioned oils admixed with organic solvents such as n-hexan, followed by removal of the solvents. The impregnation method, however, is not limited to the above.

A preferred manner of use of the cleansing and wiping composition thus prepared is, for example, a finish wiping after post-defacation wiping in the conventional manner with toilet paper etc., or on the occasion of diaper exchange. The effects of the cleansing and wiping material can be further improved by wiping the circumanal region with the cleansing material according to the invention after bathing or prior to defecation.

The following examples illustrate the invention in more detail.

EXAMPLE 1

A cleansing and wiping composition formulated as indicated in Table 1 was filled in a pressure accumulating pump bottle with 30 ml capacity. Ten persons suffering from hemorrhoids used tissue paper sprayed with the composition after defecation, and the feeling of use was investigated. The results are shown in table 1.

| | Criteria for Evaluation | | |
|---|---|---|---|
| Evaluation | Pain caused in Wiping | Refreshing Feeling | Smooth Feeling |
| ++ | Easily wiped without feeling any pain | Very refreshing and felt good | Very smooth and move lightly |
| + | Easily wiped | Refreshing | Felt smooth |
| − | Not particular difference from conventional ones or feel pain | Not particular difference from conventional ones | Not particular difference from conventional ones |
| −− | Felt severe pain | Felt bad | Sticky and felt bad |

TABLE 1

| | Results | | |
|---|---|---|---|
| | Feeling of Use* | | |
| Composition | Pain caused in wiping | Refreshing feeling | Smooth feeling |
| This Invention | | | |
| Squalane | ++ | ++ | ++ |
| Mixture consisting of equal amounts of squalane and glycerin tri-2-ethylhexanoate | ++ | ++ | ++ |
| Mixture consisting of equal amounts of jojoba oil, | ++ | ++ | ++ |

TABLE 1-continued

| | Results | | |
|---|---|---|---|
| | Feeling of Use* | | |
| Composition | Pain caused in wiping | Refreshing feeling | Smooth feeling |
| squalane and glycerin tri-2-ethylhexanoate | | | |
| Reference | | | |
| Liquid paraffin | + | − | − |
| Olive oil | + | − | − |
| Lanolin | −− | −− | −− |

*The feeling of use was indicated by average of 10 persons.

EXAMPLE 2

Eight persons, suffering from the following hemorrhoidal symptoms, but not currently using any hemorrhoid medicine, used a cleansing and wiping composition consisting of equal amounts of jojoba oil, squalane and glycerin tri-2-ethylhexanoate after each defecation over a two week period. The results are shown in Tables 2 and 3.

| Symptoms of the Users | |
|---|---|
| Excrescences often protrude at the time of defecation | 2 persons |
| Pain and hemorrhage accompanying protrusion of excrescences are sometimes experienced at the time of defecation | 4 persons |
| Pain and hemorrhage often experienced at the time of defecation | 2 persons |

TABLE 2

| Results | |
|---|---|
| Pain Experienced during Wiping | |
| Pain notably alleviated compared to before | 1 person |
| Pain was alleviated | 6 persons |
| No change | 1 person |

TABLE 3

| Ease of Withdrawal of Internal Hemorrhoid | |
|---|---|
| Came to withdraw very easily compared to before | 1 person |
| Came to withdraw easily | 5 persons |
| No change | 2 persons |

EXAMPLE 3

Degrees of skin damage caused when toilet paper produced from wastepaper (reference material) was used and when the same toilet paper sprayed with a wiping and cleansing agent consisting of equal amounts of jojoba oil, squalane and glycerin tri-2-ethylhexanoate (invention composition) was used, were evaluated according to the following method.

METHOD OF EVALUATION

The skin of the inner side of human forearm was wiped with the above reference material or the invention composition 4 times with a force of around 100 g/cm², followed by collecting the replica of the skin condition by the sump method and observing with a light microscope.

RESULTS

Figure 2:
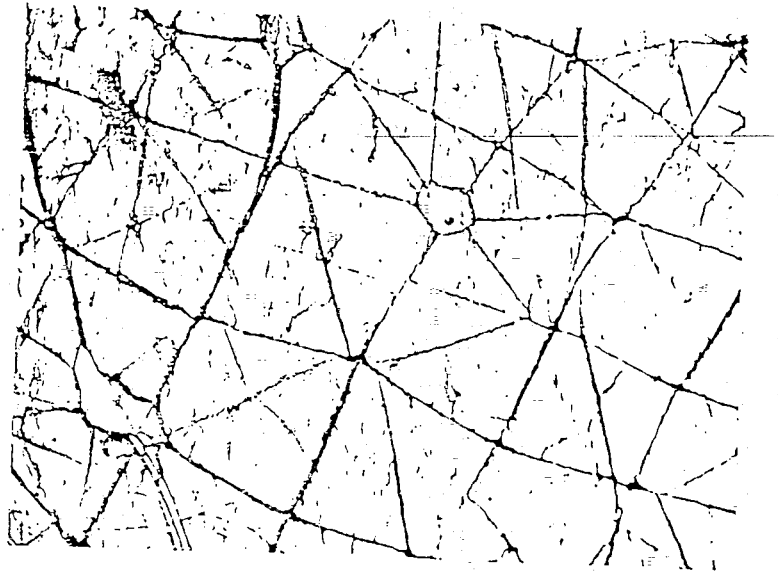
FIG. 2 is an illustration (photograph) indicating the skin condition after wiped and cleaned with the same toilet paper but sprayed with the wiping and cleansing composition of this invention.

Considerable streaks were observed on the epidermis after wiping with the reference material (FIG. 1), while almost no streaks were observed with the use of the invention composition (FIG. 2). Thus, it has been clearly demonstrated that the invention composition has an effect of preventing skin damage.

What is claimed is:

1. A product for cleansing and wiping skin, which comprises a solid support selected from the group consisting of paper, non-woven fabric, cloth, polymer film, sponge and formed plastics, wherein said support is impregnated with a cleansing composition which consists essentially of at least one oil selected from the group consisting of jojoba, natural squalane and glycerin tri-2-ethylhexanoate.

2. The product of claim 1, wherein said solid support is paper or nonwoven fabric.

3. The product of claim 2, wherein said solid support is a toilet wipe.

4. The product of claim 3, wherein said solid support is toilet paper.

5. A method of preparing a toilet wipe intended for anal application, which comprises impregnating a toilet wipe with a cleansing composition which consists essentially of at least one oil selected from the group consisting of jojoba, natural aqualane and tri-2-ethylhexanoate.

6. The method of claim 5 wherein said toilet wipe is toilet paper.

* * * * *